United States Patent [19]

Siri

[11] Plant 5,186

[45] Jan. 31, 1984

[54] MINIATURE CARNATION

[75] Inventor: Angelo J. Siri, San Francisco, Calif.

[73] Assignee: Siri Brothers Nursery, Inc., East Palo Alto, Calif.

[21] Appl. No.: 397,561

[22] Filed: Jul. 12, 1982

[51] Int. Cl.[3] ..... A01H 5/00

[52] U.S. Cl. ..... Plt./70

[58] Field of Search ..... Plt./70

*Primary Examiner*—Robert E. Bagwill

*Attorney, Agent, or Firm*—Limbach, Limbach & Sutton

[57] ABSTRACT

A miniature carnation plant having lavender-purple blossoms striped white.

4 Drawing Figures

BACKGROUND OF THE NEW PLANT

This invention comprises a new and distinct miniature carnation variety that has its own set of characteristics that set it apart from all other varieties of miniature carnations. The newly discovered variety, called "Siri's Orchid Royalette," originated as a sport of White Royalette, an unpatented variety.

The botanical classification of the new variety is Dianthus Caryophyllus Longicaulis. The commercial classification is Miniature Carnation. The plant takes the form of a bush.

Asexual propagation of the newly discovered miniature carnation variety has been made at Siri Brothers Nursery, Inc. at East Palo Alto, Calif. by taking cuttings. The cuttings so taken and grown, have consistently produced flowers that have the new and distinct characteristics hereinafter described.

DESCRIPTION OF THE DRAWINGS

This new variety of miniature carnation plant is illustrated by the accompanying drawings which show the color characteristics of the flower as nearly true as it is reasonably possible to obtain through conventional photographic procedures.

DESCRIPTION OF THE NEW PLANT

Figure 1:
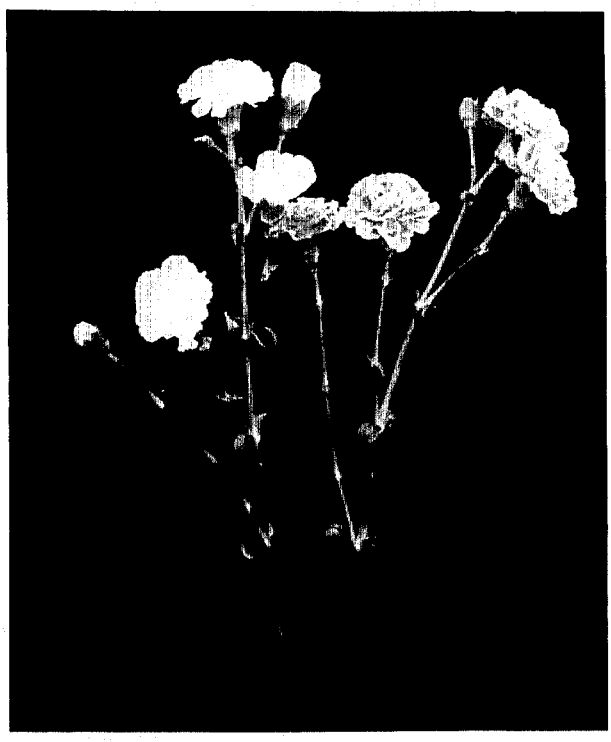
FIG. 1. PRIOR ART
FIG. 1 shows the sprays and stems of the new variety Siri's Orchid Royalette on the right and the prior White Royalette on the left.
Figure 2:
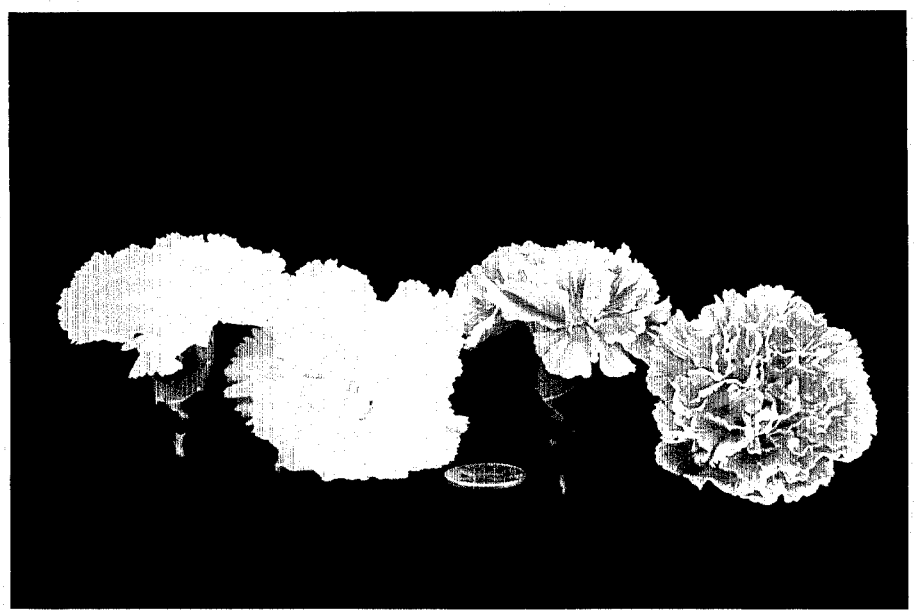
FIG. 2 shows the blooms of the new variety Siri's Orchid Royalette on the right and the prior White Royalette on the left.
Figure 3:
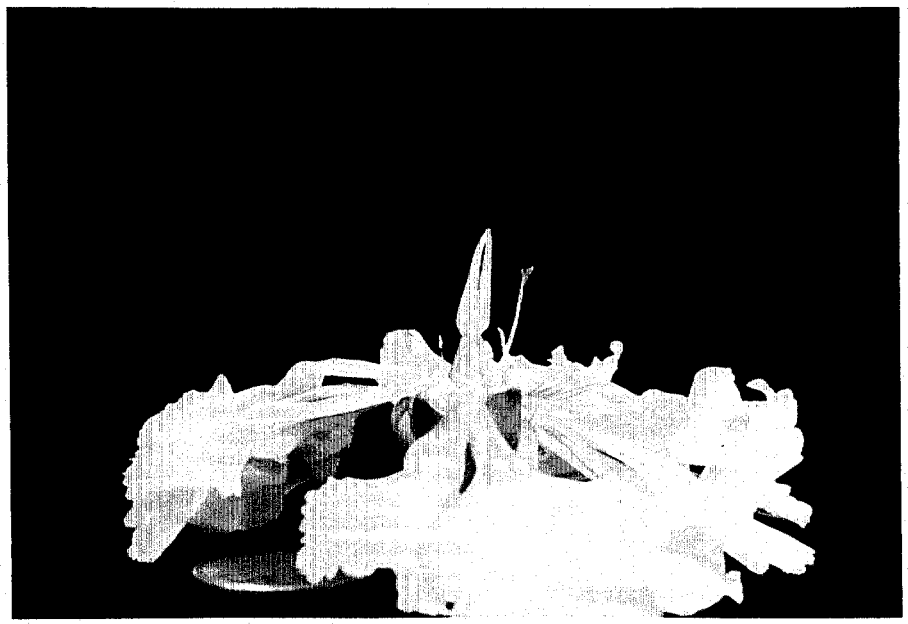
FIG. 3. PRIOR ART
FIG. 3 shows the interior of the prior White Royalette.
Figure 4:
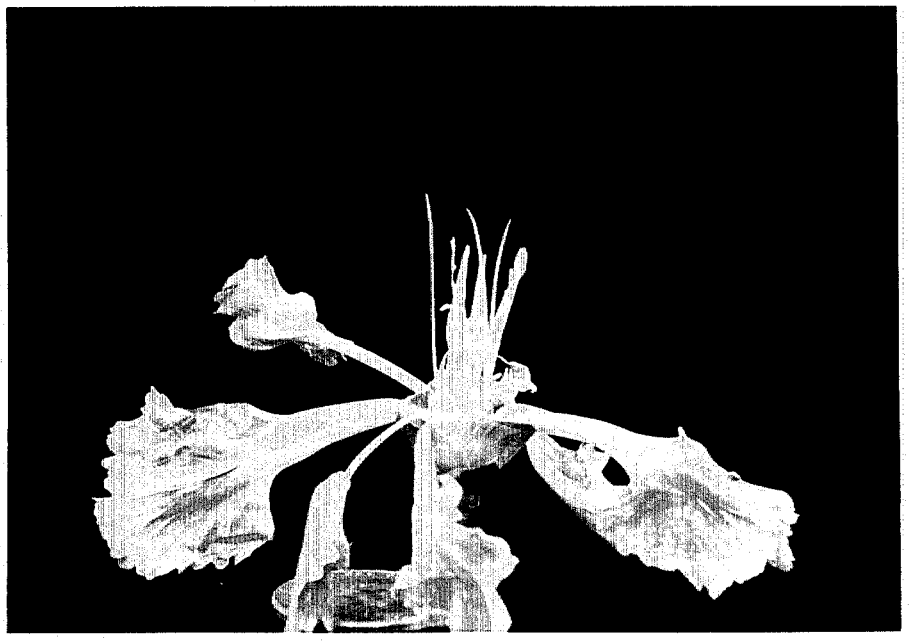
FIG. 4 shows the interior of the new variety Siri's Orchid Royalette.

The following detailed description of the new variety is based on my detailed observations of the new cultivar which were made at Siri Brothers Nursery Inc. at 940 O'Connor Street, East Palo Alto, Calif. The response time, blooming period, total vigor, and color may vary slightly with varying environmental conditions such as temperature, length of day, and light intensity. The color description is given by designation "H" for hue and "L" for lightness in color chart references designated "LCC" for Limit Color Cascade, Munsell Color, Baltimore, Md. and "RHS" for Royal Horticultural Color Chart, The Royal Horticultural Society, London, England.

GROWTH HABITS

Height: Average as compared with other varieties.
Foliage: Denser than most varieties.
Speed of growth: Average.
Root system: Average.

FOLIAGE

Leaf size:
- *Length.*—Averages $3\frac{3}{4}''$ at mid-stem.
- *Width.*—Averages 7/16" at mid-stem.

Leaf shape: Average curl with a long acuminating tip.
Leaf texture: Smooth and leathery.
Leaf color:
- *Upperside.*—RHS Green Group 139A with a whitish color over the green.
- *Underside.*—RHS Green Group 139A with a whitish color over the green.

Leaf ribs: One rib down the center from the base to the tip of the leaf.
Leaf habit: More leaf curl than average.
Leaf density: Average.

STEM

Stem strength: Excellent, above average.
Stem color: RHS Green Group 139A with a whitish color over the green.
Nodes: Average.
- *Space between nodes.*—$2\frac{3}{4}$ inches average at mid-stem.

Stem branching: Average.

BUDS

Bud shape: Oval.
Bud color: Top half LCC H-22 L-12 bottom half LCC H-22 L-10.
Average number of flowering buds per stem: 4–5.
Uniformity of bud opening: Very uniform.
Bud splitting: Very seldom.
Number of sepals per calyx: 50% of calyxs have 5; 47% of calyxs have 6; 3% of calyxs have 7.

FLOWER

Description of the color of the bloom: It is a medium lavender purple color, (LCC H-43 L-12 top of petal and LCC H-43 L-11 bottom of petal) with white stripes (RHS White Group 155B top and bottom of petal) at random in the petal and running at random lengths through the petal.

General tonality of the color: Vibrant.
Diameter of average bloom: 2½ inches.
Bloom shape: Generally round with a high center and flat outer petals.
Keeping quality: Average.
Fragrance: Very fragrant — above average.

PETALAGE

Petal texture: Soft and velvety.
Petal edge: Medium serration.
Petal color:
*Topside base of petal.*—Lavender Purple — LCC H-43 L-12 White — RHS White Group 155B.
*Topside middle of petal.*—Lavender Purple — LCC H-43 L-12 White — RHS White Group 155B.
*Topside outside of petal.*—Lavender Purple — LCC H-43 L-12 White — RHS White Group 155B.
*Underside base of petal.*—Lavender Purple — LCC H-43 L-11 White — RHS White Group 155B.
*Underside middle of petal.*—Lavender Purple — LCC H-43 L-11 White — RHS White Group 155B.
*Underside outside of petal.*—Lavender Purple — LCC H-43 L-11 White — RHS White Group 155B.
Color stability:
*Very stable.*—Only a slight reversion to parent.
Petal size:
*Average length.*—1¾ inches.
*Average width at widest point.*—1⅛ inches.
Calyx color: Top half LCC H-22 L-12, the bottom half is LCC H-22 L-10 the tips of the leaves on the bottom of the calyx are LCC H-19 L-15.

REPRODUCTIVE ORGANS

Stamen: With and without anthers.
Average length of stamen: ⅞ of an inch both with anthers and without.

Color of anthers: LCC H-48 L-6.
Color of filament: A transparent color like LCC H-22 L-1.
Pistils:
*Shape.*—100% have 2 styles.
*Number.*—One.
*Length from tip to ovary.*—Averages ¾ of an inch.
Stigma:
*Shape.*—Round located at the very tip of the style.
*Color.*—White.
Style:
*Color.*—LCC H-25 L-1 with the purple color LCC H-43 L-13 at the top third of the style in varying amounts.
Ovary:
*Shape.*—Ovid.
*Color.*—Tip LCC H-26 L-11, middle LCC H-22 L-4, bottom LCC H-23 L-1.
*Length.*—5/16 of an inch.
*Width.*—3/16 of an inch.

DISTINGUISHING CHARACTERISTICS BETWEEN THE NEW VARIETY AND PARENT

The distinguishing characteristic is the difference in color; the parent being white and the sport from the parent lavender with white striping. Also the styles of Siri's Orchid Royalette have lavender (LCC H-43 L-13) at the tips in varying amounts while the parent doesn't.

SIMILAR CHARACTERISTICS OF THE NEW VARIETY AND PARENT

All of the characteristics of both varieties are similar except for the distinguishing characterstics referred to above.

I claim:

1. A new and distinct variety of miniature carnation plant, substantially as herein shown and described.

* * * * *

PRIOR ART